United States Patent
Bae et al.

(10) Patent No.: US 9,468,616 B2
(45) Date of Patent: Oct. 18, 2016

(54) PHARMACEUTICAL COMPOSITION FOR PREVENTING OR TREATING INFLAMMATORY DISEASES OR INFECTIOUS DISEASES, CONTAINING M-3M3FBS, WHICH IS ACTIVATOR OF PHOSPHOLIPASE C, AS ACTIVE INGREDIENT

(75) Inventors: Yoe Sik Bae, Seongnam-si (KR); Sang Doo Kim, Yangsan-si (KR)

(73) Assignee: Research & Business Foundation SUNGKYUNKWAN UNIVERSITY, Suwon-si (KR)

( * ) Notice: Subject to any disclaimer, the term of this patent is extended or adjusted under 35 U.S.C. 154(b) by 89 days.

(21) Appl. No.: 14/005,737

(22) PCT Filed: Mar. 14, 2012

(86) PCT No.: PCT/KR2012/001855
§ 371 (c)(1),
(2), (4) Date: Sep. 17, 2013

(87) PCT Pub. No.: WO2012/128501
PCT Pub. Date: Sep. 27, 2012

(65) Prior Publication Data
US 2014/0005271 A1 Jan. 2, 2014

(30) Foreign Application Priority Data
Mar. 18, 2011 (KR) ........................ 10-2011-0024239

(51) Int. Cl.
| | |
|---|---|
| *A61K 31/18* | (2006.01) |
| *A61K 31/192* | (2006.01) |
| *A23L 1/30* | (2006.01) |
| *A61K 9/20* | (2006.01) |
| *A61K 9/00* | (2006.01) |
| *A61K 47/20* | (2006.01) |
| *A61K 9/08* | (2006.01) |
| *A61K 9/48* | (2006.01) |

(52) U.S. Cl.
CPC .................. *A61K 31/18* (2013.01); *A23L 1/30* (2013.01); *A61K 9/0019* (2013.01); *A61K 9/08* (2013.01); *A61K 9/2059* (2013.01); *A61K 9/4866* (2013.01); *A61K 31/192* (2013.01); *A61K 47/20* (2013.01); *A23V 2002/00* (2013.01)

(58) Field of Classification Search
None
See application file for complete search history.

(56) References Cited

U.S. PATENT DOCUMENTS

| | | |
|---|---|---|
| 2004/0038976 A1 | 2/2004 | Fleming et al. |
| 2004/0220268 A1 | 11/2004 | Bae et al. |

OTHER PUBLICATIONS

Komatsu et al. (Early Human Development 65 (2001) pp. 11-19).*
International Search Report issued Oct. 31, 2012, in counterpart International Application No. PCT/KR2012/001855. (2 pages in English).
Bae, Yoe Sik, et al. "Identification of a Compound That Directly Stimulates Phospholipase C Activity." Molecular Pharmacology 63.5 (2003): 1043-1050.
Lee, Youl-Nam, et al. "The novel phospholipase C activator, m-3M3FBS, induces monocytic leukemia cell apoptosis." Cancer letters 222.2 (2005): 227-235.
Kim, Sang Doo, et al. "Phospholipase C Activator m-3M3FBS Protects against Morbidity and Mortality Associated with Sepsis." The Journal of Immunology 189.4 (2012): 2000-2005.

* cited by examiner

*Primary Examiner* — Kortney L Klinkel
*Assistant Examiner* — William Lee

(57) ABSTRACT

Provided herein are a composition for preventing or treating inflammatory diseases or infectious diseases which contains m-3M3FBS or a pharmaceutically available salt thereof as an active ingredient, and health supplements for improving or preventing inflammatory diseases or infectious diseases which contain m-3M3FBS. Since m-3M3FBS has a microbicidal effect, inhibition of apoptosis, and inhibition of LPS-involved signal transduction which enables to effectively treat or prevent inflammatory diseases or infectious diseases, so that it may be effectively used as medicine or health supplements for treating or preventing inflammatory diseases or infectious diseases.

5 Claims, 6 Drawing Sheets

PHARMACEUTICAL COMPOSITION FOR PREVENTING OR TREATING INFLAMMATORY DISEASES OR INFECTIOUS DISEASES, CONTAINING M-3M3FBS, WHICH IS ACTIVATOR OF PHOSPHOLIPASE C, AS ACTIVE INGREDIENT

CROSS REFERENCE TO RELATED APPLICATIONS

This application is a National Stage of International Application No. PCT/KR2012/001855 filed Mar. 14, 2012, claiming priority based on Korean Patent Application No. 10-2011-24239 filed Mar. 18, 2011 the contents of all of which are incorporated herein by reference in their entirety.

TECHNICAL FIELD

The present invention relates to a composition for preventing or treating inflammatory diseases or infectious diseases, which contains m-3M3FBS of Formula 1, or a pharmaceutically available salt thereof as an active ingredient. More particularly, the present invention relates to a composition for preventing or treating inflammatory diseases or infectious diseases, which contains m-3M3FBS of Formula 1, or a pharmaceutically available salt thereof as an active ingredient since the m-3M3FBS treated to cells and animal models has an influence on decrease in mortality, decrease in pulmonary inflammation, induction of death of bacteria and production of hydroperoxides in phagocytes, inhibition of apoptosis, and production of cytokine-induced inflammation.

BACKGROUND ART

Inflammation refers to a pathological state of abscess formed by infection from external sources of infection (bacteria, fungi, viruses, various types of allergens, etc.). Specifically, when external microbes infect a specific tissue and proliferate, leukocytes of the living organism recognize and actively attack the external microbes. Dead leukocytes caused by the above process are accumulated in the tissue infected by the microbes, and cell debris of the infected microbes killed by the leukocytes fuses with the infected tissue, which results in formation of abscesses. Treatment of an abscess caused by inflammation can be stimulated by an anti-inflammatory action, which stimulates the treatment of inflammation by suppressing proliferation of infected microbes using an antimicrobial agent or by activating macrophages ingesting foreign substances accumulated in the abscess to accelerate a function of the macrophages digesting and excreting the foreign substances.

Generally, the inflammatory response is a process of a defense mechanism in a living organism to repair and regenerate from damage caused by an invasion causing an organic change in cells or tissues of the living organism, and in this process, various tissue cells and immune cells of local blood vessels and body fluids are used. Normally, inflammatory response induced by external infectious microbes is a defense system for protecting a living organism, but when an abnormal excessive inflammatory response is induced, various diseases are caused, which are called inflammatory diseases. The inflammatory diseases are life-threatening diseases caused when various inflammation-mediated substances secreted from target cells activated by external stimuli induce amplification and sustainment of inflammation, and include acute bronchitis, chronic bronchitis, acute bronchiolitis, chronic bronchiolitis, sepsis, septic shock, acute respiratory distress syndrome, multiple organ failure, and chronic obstructive pulmonary disease.

The occurrence of various inflammatory diseases is associated with activation of macrophages and excessive production of inflammatory factors caused thereby, and as a representative inflammatory factor, IL-β, tumor necrosis factor (TNF)-α, or nitrogen oxide (NO) is used.

Lipopolysaccharide (LPSs) of the inflammatory substances for the inflammatory response is a substance for forming a cell surface of Gram-negative bacteria, and interacts with immune cells such as leukocytes and is associated with regulation of inflammatory cytokines.

Particularly, one of the inflammatory diseases, sepsis, refers to the occurrence of systemic inflammatory response syndrome (SIRS) from several microorganisms. Sepsis is caused by the influx of microbes having a symbiotic relationship with the adjacent tissues from the gastrointestinal tract or skin, and partial infections of the genitourinary tract, bile, lung, or gastrointestinal tract can cause blood infections. In addition, such microbes may directly infiltrate into blood by intravenous injection. That is, reactions of the host, which is a human, caused by microbial infection appear in various types of inflammatory responses, for example, high or low fever, chills, tachycardia, tachypnea, etc. Sepsis is a very deadly disease that can develop into severe sepsis, septic shock, or a multiple organ dysfunction syndrome (MODS) in which dysfunctions of the lung, kidney, liver, or circulatory system arise as complications and that can lead to death when causes of the sepsis are not quickly and accurately diagnosed early.

Sepsis can occur in all people infected with microbes. Among such people, sepsis occurs more frequently, particularly, in very young infants, the elderly, or hospitalized patients such as people with weak immune systems, people with scars or wounds caused by traffic accidents, alcoholics or drug addicts, or patients who are receiving treatment with catheters in a hospital.

It is reported that sepsis is a representative incurable disease leading to death at a rate of 20 to 50%, and contributes to severe sepsis for 18 million or more people every year in the world, and has also become a major cause of death of approximately 1,400 people every day, which is 5 to 10 times the rate of colorectal cancer and breast cancer. Every year, 215,000 or more people in the United States, and 135,000 or more people in Europe die because of sepsis, which, along with cancer, is among the top 10 causes of death in the United States. The situation is further complicated by phenomena such as aging, prolonging of life of chronically-ill patients, AIDS, etc., and such phenomena are also expected to increase in Korea.

Sepsis is caused by various microorganisms, for example, also by fungi or viruses, but mostly by bacteria. According to the blood culture for 30 to 60% of sepsis patients and 60 to 80% of septic shock patients, gram-negative bacteria are shown in approximately two-thirds of the patients, and gram-positive bacteria are only shown in 10 to 20% of the patients. Recently, there is a tendency of an increase in gram-positive bacteria over gram-negative bacteria as a major cause of sepsis.

It has been disclosed in recent research that septic mortality closely relates to the inability to regulate an inflammatory reaction resulting from intrinsic immune system disorders in early sepsis. In addition, sepsis is accompanied by excessive apoptosis of lymphocytes, and accordingly, multi-organ failure occurs. The level of cytokines is significantly changed, and pro-inflammatory cytokines, that is, TNF-α and IL-β, are significantly increased. Therefore, microbicidal action, prevention of imbalance of cytokines, or inhibition of the apoptosis of lymphocytes or cell death should be targeted in the treatment of sepsis.

Phospholipase C (PLC) is an enzyme for hydrolyzing phospholipids by cleaving a phosphate group. Phosphatidylinositol-specific PLC (PI-PLC) is one of the information-transforming phospholipases catalyzing the hydrolysis of phosphatidylinositol 4,5-bisphosphate ($PIP_2$) in a signal transduction pathway within phospholipids of a cell membrane to produce second messengers (inositol-1,4,5-trisphosphate and 1,2-diacylglycerol). PLC plays an important role in regulation of leukocyte activation by various extracellular stimuli, and the increase in activation of intracellular calcium and protein kinase C is associated with intracellular signal transduction, which includes activation of phospholipase $A_2$, phospholipase D, and mitogen-activated protein kinase (MAPK). In addition, PLC-involved signal transduction regulates cellular responses including production, secretion, and maintenance of superoxides.

It is known that PLC is very important as a cell signaling substance, but its pathophysiological role has not yet been clearly identified. Accordingly, the inventors of the present invention developed m-3M3FBS, which is a direct regulator of PLC, through screening of small molecule libraries, and confirmed a pharmaceutical role and effect of m-3M3FBS in inflammatory diseases and infectious diseases, thereby inventing a pharmaceutical composition for treating or preventing and health supplements for improving or preventing inflammatory diseases or infectious diseases.

DISCLOSURE

Technical Problem

The present invention is directed to providing a composition for preventing or treating inflammatory diseases or infectious diseases, which contains m-3M3FBS or a pharmaceutically available salt thereof as an active ingredient.

The present invention is also directed to providing health supplements for improving or preventing inflammatory diseases or infectious disease, which contain m-3M3FBS.

Technical Solution

To achieve the above object, the present invention provides a composition for preventing or treating inflammatory diseases or infectious diseases, which contains m-3M3FBS of Formula 1 or a pharmaceutically available salt thereof as an active ingredient.

[Formula 1]

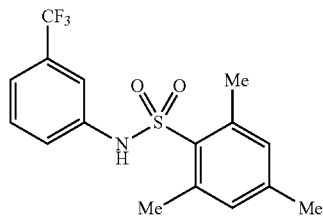

In addition, in the present invention features that m-3M3FBS or pharmaceutically available salt thereof is an activator of PLC.

The inflammatory disease of the present invention may preferably be at least one selected from the group consisting of acute bronchitis, chronic bronchitis, acute bronchiolitis, chronic bronchiolitis, sepsis, septic shock, acute respiratory distress syndrome, multiple organ failure, and chronic obstructive pulmonary disease, and more preferably be sepsis or septic shock.

The present invention features that m-3M3FBS or pharmaceutically available salt thereof is associated with microbicidal action, inhibition of the apoptosis of leukocytes, or inhibition of LPS-involved signal transduction.

The composition of the present invention may further include a carrier, an excipient or a diluent conventionally used in the preparation of a pharmaceutical composition. In addition, the composition of the present invention may be prepared or used in combination with a drug selected from the group consisting of anti-inflammatory drugs, antipyretic & analgesics, anticoagulants, antibiotics, antimicrobial agents, and antiallergic drugs.

Furthermore, the present invention provides health supplements for improving or preventing inflammatory diseases or infectious diseases which contain m-3M3FBS of Formula 1.

Advantageous Effects

According to the present invention described above, since m-3M3FBS has a microbicidal effect, inhibition of apoptosis, and inhibition of LPS-involved signal transduction that enables to treat or prevent inflammatory diseases and infectious diseases, it can be effectively used as medicines or health supplements for treating or preventing inflammatory diseases and infectious diseases.

DESCRIPTION OF DRAWINGS

FIG. 4B). Compared with the CLP+PBS, values are at *P<0.05 and ***P<0.001.

IDEAL MODEL FOR INVENTION

Figure 1:
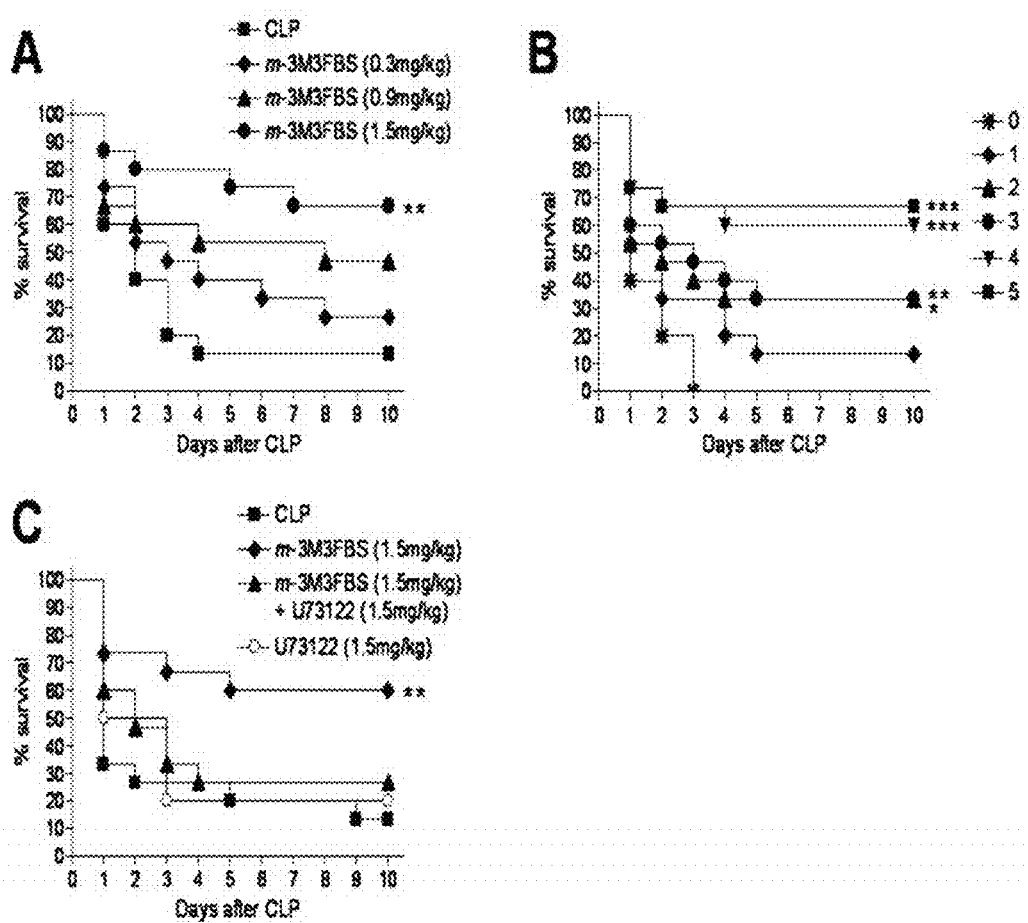
FIG. 1 is a diagram showing an effect of m-3M3FBS to reduce sepsis-induced mortality, in which (A) shows results obtained by injecting various concentrations of m-3M3FBS after CLP into CLP mice four times at intervals of after 2, 14, 26, and 38 hours, (B) shows results obtained by subcutaneously injecting m-3M3FBS (1.5 mg/kg) into CLP mice 0, 1, 2, 3, 4, and 5 times, and (C) shows results obtained by injecting U-73122 (1.5 mg/kg) before 2 hours of CLP treatment. The U-73122 (1.5 mg/kg) was injected 4 times after 2 hours of m-3M3FBS (1.5 mg/kg) treatment at intervals of 12 hours. Data is represented as average±standard deviations, and values compared with the vehicle control are at P<0.01 and *P<0.001. A sample size is n=15-24 (A-C) mice/group.

Hereinafter, the present invention will be described in further detail.

The present invention provides a composition for preventing or treating inflammatory diseases or infectious diseases, which includes m-3M3FBS of Formula 1 or a pharmaceutically available salt thereof as an active ingredient.

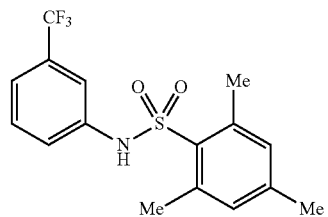

[Formula 1]

The m-3M3FBS or pharmaceutically available salt thereof of the present invention is an activator of phospholipase C.

The m-3M3FBS represented by Formula 1 may be used in the form of a pharmaceutically available salt, which may be an acid addition salt formed by pharmaceutically available free acid.

The term "pharmaceutically available salt" refers to any organic or inorganic added salt of the base compound of Formula 1 which is used in such a concentration that exhibits relatively non-toxic and harmless effective actions to a patient, and which has side effects that do not decrease advantageous effects of the base compound of Formula 1. The salt may use inorganic acid and organic acid as free acid, in which the inorganic acid may be hydrochloric acid, hydrobromic acid, nitric acid, sulfuric acid, perchloric acid, or phosphoric acid, and the organic acid may be citric acid, acetic acid, lactic acid, maleic acid, fumaric acid, gluconic acid, methane sulfonic acid, gluconic acid, succinic acid, tartaric acid, galacturonic acid, embonic acid, glutamic acid, aspartic acid, oxalic acid, (D) or (L) malic acid, maleic acid, methane sulfonic acid, ethane sulfonic acid, 4-toluene sulfonic acid, salicylic acid, citric acid, benzoic acid, or malonic acid. In addition, these salts include alkali metal salts (such as sodium salts and potassium salts) and alkaline earth metal salts (calcium salts, magnesium salts, etc.). For example, as the acid added salt, acetate, aspartate, benzoate, besylate, bicarbonate/carbonate, bisulfate/sulfate, borate, camsylate, citrate, edisilate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methyl sulfate, naphthalate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate, aluminum, arginine, benzathine, calcium, choline, diethylamine, diolamine, glycine, lysine, magnesium, meglumine, olamine, potassium, sodium, tromethamine, and zinc salt can be added, and among these, hydrochloride or trifluoroacetate is preferably used.

In addition, m-3M3FBS represented as Formula 1 of the present invention not only includes pharmaceutically available salt, but also any of salts, isomers, hydrates and solvents that can be prepared by a conventional method.

The "inflammation" referred to herein generally appears as a result of a localized protective reaction of body tissues against foreign substances or host intrusion caused by harmful stimuli. The cause of inflammation may be an infectious cause such as bacteria, viruses, and parasites, a physical cause such as burns or irradiation, chemicals such as toxins, drugs or industrial reagents, immune responses such as allergic and autoimmune reactions, or disorders associated with oxidative stress. Examples of the inflammatory diseases of the present invention are acute bronchitis, chronic bronchitis, acute bronchiolitis, chronic bronchiolitis, sepsis, septic shock, acute respiratory distress syndrome, multiple organ failure, or chronic obstructive pulmonary disease.

The infectious diseases of the present invention include infectious disease caused by practically all kinds of infectious factors which contains bacteria, viruses, parasites and fungi. For example, the present invention provides a composition for preventing or treating infectious diseases from bacterial infection caused by *Pseudomonas, Excherichia, Klebsiella, Enterobacter, Proteus, Serratia, Candida, Staphylococci, Streptococci, Chlamydia, Mycoplasma* and a variety of other species. Exemplary viral symptoms that can be treated according to the present invention include, symptoms caused by, for example, influenza virus, adenovirus, parainfluenza, rhinovirus, respiratory syncytial virus (RSV), herpesvirus, or cytomegalovirus, and for example, hepatitis B or C virus. As exemplary fungi, *Aspergillis, Candida albicans*, or *Cryptococcus neoformans* are included.

The m-3M3FBS which is an active ingredient in the composition for preventing or treating inflammatory diseases or infectious diseases according to the present invention, is associated with microbicidal action, inhibition of leukocytes apoptosis or inhibition of LPS-involved signal transduction.

The "apoptosis" referred to herein is natural death of cells as cell membranes or organelles are maintained in a normal shape, and the nuclear chromatin is condensed, resulting in overall contraction and fragmentation of the cells. In this process, DNA in the nucleus is fragmented.

The "lipopolysaccharide (LPS)" referred to herein is the major component of the outer membrane that surrounds the peptidoglycans of the gram-negative bacteria's surface, and approximately $3 \times 10^5$ molecules (20 to 30% of the surface) exist per cell. LPS acts on inflammatory cells, endothelial cells and etc. of the host and stimulates secretion of cytokines.

A preferable dose of the pharmaceutical composition of the present invention depends on the condition and weight of a patient, the severity of a disease, a drug type, an administration route, and duration, and may suitably be selected by one of ordinary skill in the art. However, for a beneficial effect, the pharmaceutical composition of the present invention may be administered at 0.001 to 1000 mg/kg, preferably 0.1 to 1000 mg/kg, and more preferably 1 to 1000 mg/kg, a day. The optimum dose is 1.5 mg/kg. The administration may be performed once or divided several times a day.

The present invention includes a composition that features further including a carrier, an excipient, or a diluent that is conventionally used in preparation of the pharmaceutical composition.

The pharmaceutical composition of the present invention may be formulated into oral dosage form including powder, granules, tablet, capsule, suspension, emulsion, syrup, aerosol, external application, a suppository, or a sterilized injectable solution and used.

Carrier, excipient and diluent that can be included in the above pharmaceutical composition are lactose, dextrose, sucrose, sorbitol, mannitol, xylitol, erythritol, maltitol, starches, gum acacia, alginate, gelatin, calcium phosphate, calcium silicate, cellulose, methyl cellulose, microcrystalline cellulose, polyvinyl pyrrolidone, water, methyl benzoate, propylhydroxy benzoate, talc, magnesium stearate, or mineral oil.

When medicine is prepared, common diluent or excipient such as filler, extender, binder, wetting agent, disintegrating agent, or surfactant are used for preparation. The composition is formulated using a usually-used diluent or excipient.

The solid formulations for oral administration include tablets, pills, powder, granules, and capsules and such solid formulations are formulated by mixing at least one excipient, for example, starch, calcium carbonate, sucrose, lactose, or gelatin to the extract. In addition, besides simple excipient, lubricants such as magnesium stearate, talc, etc., are also used. As liquid formulations for oral administration, suspensions, liquids, emulsions, syrups, and etc. are included, and besides simple diluents that are frequently used such as water, liquid paraffin, and etc., various excipients, for example, wetting agents, sweeteners, fragrances, and preservatives, may be included. Formulations for parenteral administration include sterilized aqueous solutions, non-aqueous solvents, suspensions, emulsions, freeze-dried formulations, and suppositories. For non-aqueous solvent or suspension, propylene glycol, polyethylene glycol, vegetable oils such as olive oil, or injectable esters such as ethyloleate may be used. For the base material of suppositories, witepsol, macrogol, tween 61, cacao butter, laurinum, or glycerogelatin may be used.

The composition of the present invention may be administered through various routes to mammals such as rats, mice, livestock, and humans. All methods of administration may be expected, for example, it may be administered by oral, rectal, intravenous, intramuscular, subcutaneous, intrauterine, or intracerebral injection.

In addition, the present invention provides a pharmaceutical composition for treating inflammatory diseases or infectious diseases, which is prepared or used in combination with a drug selected from the group consisting of anti-inflammatory agents, antipyretic-analgesics, blood clotting inhibitors, antibiotics, antimicrobial agents, and antiallergic agents.

The present invention provides health supplements for improving or preventing inflammatory diseases or infectious diseases, which contain m-3M3FBS of Formula 1.

Hereinafter, preparation examples of the composition will be explained, but they are provided not to limit the present invention, but merely to explain the present invention in detail.

Preparation Example 1

Preparation of Injectable 100 mg m-3M3FBS
3.0 mg of sodium metabisulfite
0.8 mg of methylparaben
0.1 mg of propylparaben
Appropriate amount of sterilized distilled water for injection Parental injection is prepared by mixing the above components, adjusting a volume of the mixture to 2 ml by a conventional method, charging the mixture into a 2 ml ampoule, and sterilizing the ampoule.

Preparation Example 2

Preparation of Tablet 200 mg m-3M3FBS
100 mg of lactose
100 mg of starch
Appropriate amount of magnesium stearate
A tablet is prepared by mixing the above components, and compressing the mixture in the form of a tablet by a conventional method.

Preparation Example 3

Preparation of Capsule 100 mg m-3M3FBS
50 mg of lactose
50 mg of starch
2 mg of talc
Appropriate amount of magnesium stearate A capsule is prepared by mixing the above components, and charging the resulting mixture into a gelatin capsule by a conventional method.

Preparation Example 4

Preparation of Liquid 1000 mg of m-3M3FBS
20 g of sugar
20 g of isomerizer
Appropriate amount of lemon zest vPurified water is added and adjusted to 1000 ml. A liquid is prepared according to a conventional method of preparing a liquid by mixing the above components, charging the mixture into a brown bottle, and sterilizing.

Preparation Example 5

Blending with Other Active Ingredients (Preparation of Tablet)

20 mg of m-3M3FBS
200 mg of ketoprofen (anti-inflammatory drug)
100 mg of lactose
100 mg of starch
Appropriate amount of magnesium stearate A tablet is prepared by mixing the above components together and compressing the mixture in the form of a tablet according to a conventional method of preparing a tablet.

Preparation Example 6

Preparation of Health Foods 1000 mg of m-3M3FBS
Appropriate amount of vitamin mixture
70 μg of vitamin A acetate
1.0 mg of vitamin E
0.13 mg of vitamin B1
0.15 mg of vitamin B2
0.5 mg of vitamin B6
0.2 μg of vitamin B12
10 mg of vitamin C
10 μg of biotin
1.7 mg of nicotinic acid amide
50 μg of folic acid
0.5 mg of calcium pantothenate
Appropriate amount of mineral mixture
1.75 mg of ferrous sulfate
0.82 mg of zinc oxide
25.3 mg of magnesium carbonate
15 mg of potassium phosphate
55 mg of dicalcium phosphate
90 mg of potassium citrate
100 mg of calcium carbonate
24.8 mg of magnesium chloride The above composition ratio of vitamin and mineral mixture according to a preferable example with relatively suitable components for health foods, but the blending ratio may be optionally modified, and after the above components are mixed according to a conventional method of preparing health foods, it is granulated, and it can be used for preparing health food composition according to a conventional method.

Hereinafter, the present invention will be described in further detail with reference to Examples. Examples are merely provided to explain the present invention in further detail, and it will be apparent to those of ordinary skill in the art that the scope of the present invention is not limited to the following Examples.

Example 1

1-1: Sample—Animal Models

Male WT ICR mice were used as test models. All tests involving animals were performed according to the guidelines, and received the approval of Institutional Review Committee for Animal Care and Use from Dong-a University. For cecal ligation and puncture (CLP), the mice were anesthetized by intraperitoneal injection of pentothal sodium (50 mg/kg), and the cecum was exposed through midline incision of the abdomen. The cecum was ligated at a terminal end of the ileocecal valve, and the surface was perforated twice, or once to measure cytokine production using a 22-gauge needle, and the abdomen was closed. The control (sham) CLP mice underwent the same process as described above, but the cecum was not ligated or punctured. The survival rate was observed for 10 days daily.

1-2: Detection of In Vivo Microbicidal Action 24 hours after the CLP, peritoneal lavage fluid was harvested, and was incubated overnight in a blood-agar base plate (Trypticase Soy Agar Deeps, Becton Dickinson) at 37° C. CFUs were estimated by counting bacteria colonies formed in the blood-agar base plate (Trypticase Soy Agar Deeps, Becton Dickinson).

1-3: Quantification of Pulmonary Edema

The degree of pulmonary edema was identified by measuring a wet-to-dry (W/D) ratio of the lung. The wet weight of the harvested cells was measured, and the cells were placed in an oven at 60° C. for 48 hours, and the dry weight of the cells was measured, thereby obtaining the W/D ratio.

1-4: Histological Observation 2 hours after the mice underwent CLP, PBS or m-3M3FBS was administered at a concentration of 1.5 mg/kg. 24 hours after the surgery, the mice were euthanized, and the lung was fixed, cut, and stained with hematoxylin and eosin to perform morphological analysis.

1-5: Isolation of Neutrophils and Detection of Hydrogen Peroxide ($H_2O_2$)

Neutrophils of mice were isolated from peripheral blood using Histopaque-1077 solvent (Sigma), and neutrophils isolated from a normal mouse were stimulated by treating various concentrations of m-3M3FBS for 10 minutes in the presence of cytochalasin B (5 μm). To examine the role of PLC, the neutrophils were preincubated for 30 minutes in the presence of U-73122 (10 µm) or an inactive analog thereof, that is, U-73343, and then m-3M3FBS (10 µm) was added thereto for 10 minutes. $H_2O_2$ obtained from a supernatant was analyzed using $H_2O_2$ Molecular Probes.

1-6: Microbicidal Action of Neutrophils

Neutrophils were incubated for 1 hour at a 13-mm plastic cover slip on a 60-mm plastic petri dish ($1 \times 10^6$ neutrophils/cover slip) at 37° C. Unattached neutrophils were removed by PBS washing, and the attached neutrophils were incubated with $10^6$ of opsonized *E. coli* for 20 minutes. Microbes ingested by neutrophils were incubated for 30 minutes at various concentrations of m-3M3FBS or vehicles, and changes of the microbes before and after incubation were examined. A percentage of dead microbes was calculated by $100 \times (1 -$ the number of CFU after m-3M3FBS stimulation/ the number of CFU before m-3M3FBS stimulation). To examine a role of the PLC, the neutrophils were preincubated with U-73122 (10 µM) or an inactive analog thereof, that is, U-73343 (10 µM), for 30 minutes, and incubated with m-3M3FBS (10 µM) for 30 more minutes.

1-7: TUNEL Assay

The TUNEL assay was performed on tissue fragments embedded in paraffin, and the fragments were subjected to permeation of Triton X-100 at 4° C. for 2 minutes, and immersed in a TdT enzyme and a digoxigenin-dUTP reaction buffer (TUNEL) reagent for 60 minutes at 37° C. A percentage of apoptotic cells (TUNEL-positive cells) was determined by counting 500 splenocytes, which were observed using an optical microscope.

1-8: Immunostaining

Immunostaining was performed on the paraffin-embedded tissue fragments. The fragments were incubated with primary antibodies (Cell Signal transduction) in response to fragmented capase-3, and stained with fluorescent pigment-fused secondary antibodies.

1-9: Detection of Cytokines

To detect production of CLP-inducing cytokines in peritoneal lavage fluid, m-3M3FBS was treated 2, 14, 26, or 38 hours after CLP. The peritoneal lavage fluid was harvested at various points of time from 4 to 72 hours after the CLP, and expression of cytokines in the peritoneal fluid was detected by ELISA (BD Biosciences Pharmingen).

1-10: In vitro Secretion of Cytokines In Neutrophils

Mouse neutrophils ($3 \times 10^6$ cells/0.3 ml) were incubated in a 24-well plate containing 10% FBS-contained RPMI 1640 medium, and placed in 5% $CO_2$ incubator at 37° C. Then, the neutrophils were incubated with LPS (100 ng/ml) for 6 hours in the presence or absence of m-3M3FBS (10 µM). The LPS (100 ng/ml) was treated to the cells after 30 minutes, and the cell-free supernatant was harvested by centrifugation, and the production of IL-1 or TNF-α was detected by ELISA (BD Biosciences Pharmingen) according to the manufacturer's instructions.

Example 2

Administration of m-3M3FBS Reduces Mortality Induced by CLP

The effect of m-3M3FBS on sepsis of CLP mouse models was examined by the method as described above. The survival rate of the mice was significantly decreased after 2 or 3 days of CLP (FIG. 1A). After CLP, various concentrations of m-3M3FBS were injected, resulting in significant decrease in the mortality of the mice (FIG. 1A). Compared to a vehicle-injected control, when 0.9 or 1.5 mg/kg of m-3M3FBS was injected, the mortality of the mice was significantly increased (FIG. 1A). In terms of injection frequency, when 1.5 mg/kg of m-3M3FBS was injected after 2 hours of CLP, and further injected three or four times at intervals of 12 hours, the survival rate was significantly improved (FIG. 1B). Based on these results, a subsequent experiment was performed by injecting 1.5 mg/kg of m-3M3FBS 2 hours after the CLP, and further injecting the m-3M3FBS 3 times at intervals of 12 hours. An experiment was performed to examine the role of PLC with respect to the m-3M3FBS-induced survival rate in the CLP mouse model. When a PLC-selective inhibitor, U-73122 or an inactive analog, that is, U-73343, was treated within a period of injecting the m-3M3FBS, the U-73122 completely prevented the increase in the m-3M3FBS-induced survival rate, but the inactive analog did not (FIG. 1C).

Example 3 m-3M3FBS-Induced Survival Rate is Associated with Inflammation of the Lung

Figure 2:
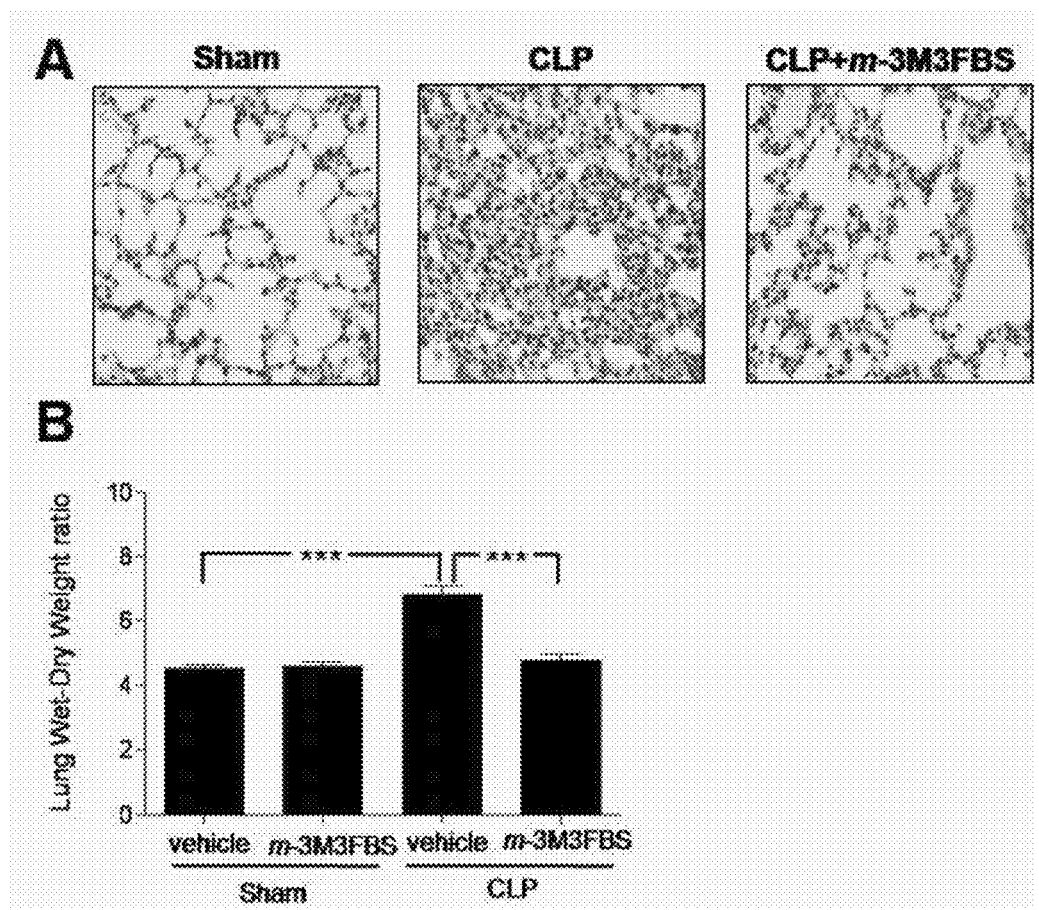
FIG. 2 is a diagram showing an effect of m-3M3FBS on inflammation in lungs. (A) shows results obtained from injecting CLP treated PBS or m-3M3FBS (1.5 mg/kg) at intervals of 2 hours and 14 hours. Mice were euthanized 24 hours after surgery. The lungs were stained with hematoxylin and eosin (magnification, ×100), and data was obtained from 8 mice per group. In (B) m-3M3FBS (1.5 mg/kg) was CLP treated and then subcutaneously injected 4 times after 2 and 14 hours, and lungs of ICR mice were treated with CLP, and after 24 hours, W/D weight ratio was measured. Data is represented as average±standard deviations (n=16; ***P<0.001).

Morphological changes caused by inflammation in the lungs were examined by hematoxylin and eosin staining CLP induced many inflammatory responses in the lung (FIG. 2A). The lung of the CLP mouse had congestion, and extensive thrombotic lesions. When m-3M3FBS was treated, it was observed that the symptoms were significantly decreased. In addition, a W/D weight ratio, that is, the indicator of the inflammation in the lung, was checked, and in a PBS-treated CLP-induced mouse, the ratio was drastically increased, but when m-3M3FBS was treated, the indicator was significantly decreased (FIG. 2B).

Figure 3:
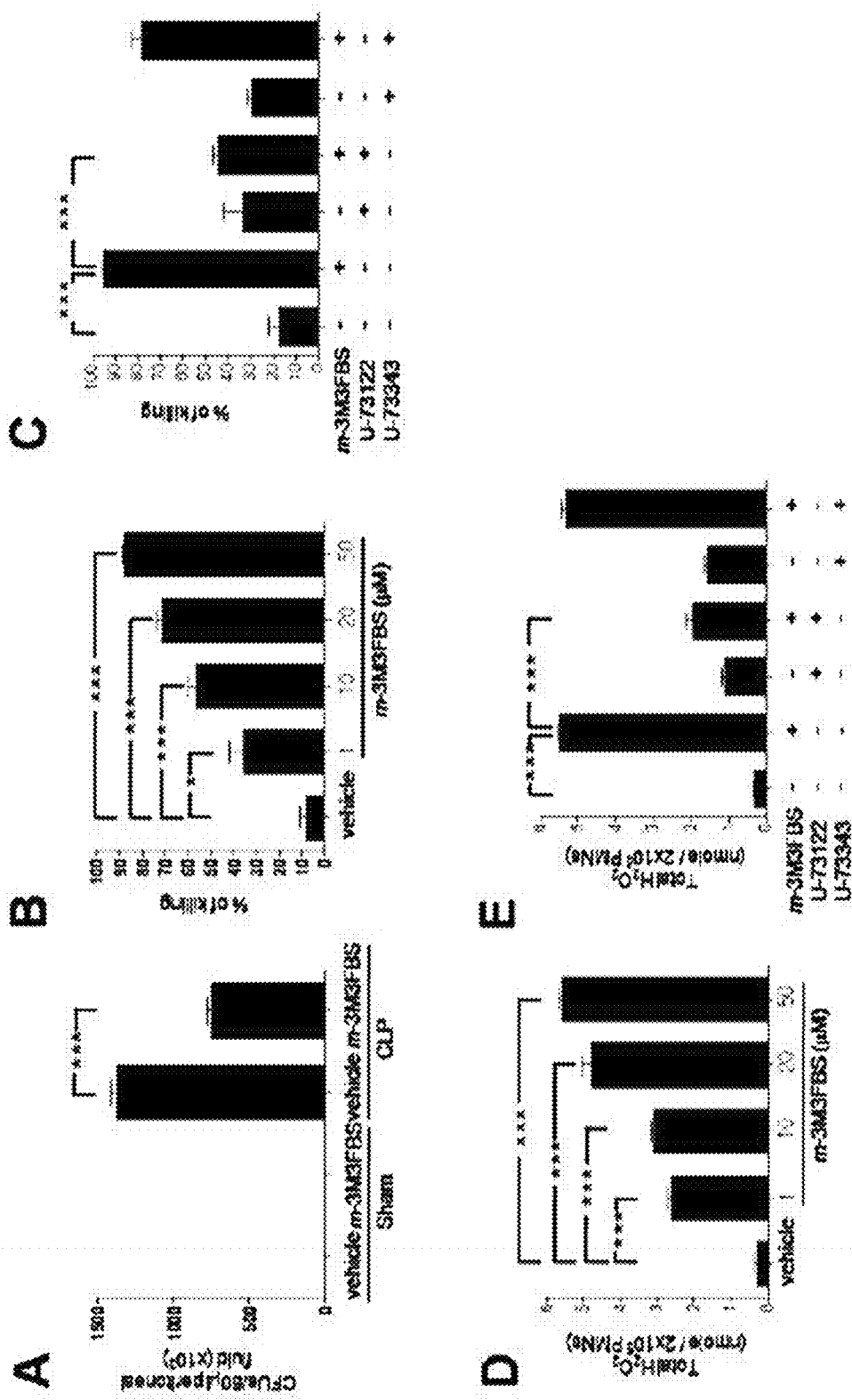
FIG. 3 is a graph showing that m-3M3FBS stimulates microbicidal actions in vivo and in vitro by production of $H_2O_2$. In (A), m-3M3FBS (1.5 mg/kg) was CLP treated and subcutaneously injected into mice four times after 2 and 4 hours. Peritoneal lavage fluid was harvested 24 hours after the injection of the control, CLP or CLP+m-3M3FBS (1.5 mg/kg), and incubated overnight in a blood-agar based plate at 37° C., and then the number of colony forming units (CFUs) was counted. (B) shows results obtained by incubating attached neutrophils with $10^6$ of opsonized E. coli for 1 hour, and then treating PBS or m-3M3FBS (1 to 50 µm) thereto. (C) shows results obtained by treating U-73122 (10 µm) or U-73343 (10 µm), injecting m-3M3FBS (50 µm) after 30 minutes, and examining living cells. (D) shows results obtained by treating PBS (vehicle) or m-3M3FBS (1 to 50 µm) to the neutrophils. (E) shows results obtained by treating U-73122 (10 µm) or U-73343 (10 µm), and then additionally treating m-3M3FBS (50 µm). A production amount of $H_2O_2$ in the neutrophils was detected using a $H_2O_2$ test kit. Data is represented as average±standard deviations (n=8 in A and B, and n=16 in C and D; *P<0.05 and ***p<0.001).

Example 4 m-3M3FBS Induces Death of Bacterial Production of Hydrogen Peroxide in Macrophages Since CLP-induced mortality was closely related to the number of colonies of bacteria in peritoneal fluid, an effect of m-3M3FBS on death of bacteria in the peritoneal fluid was examined. After 24 hours of CLP treatment, when the m-3M3FBS was treated, the number of colonies of bacteria in the abdominal cavity decreased 55% (FIG. 3A). To examine whether the microbicidal action was or was not increased by in vitro m-3M3FBS treatment, mouse neutrophils were incubated with *E. coli* for 30 minutes to ingest, and then 1 to 50 µm of m-3M3FBS was injected. The microbicidal action of the neutrophils was significantly increased in a direction proportional to the concentration (FIG. 3B). After the mouse neutrophils were preincubated with the PLC selective inhibitor, U-73122, when m-3M3FBS was added, m-3M3FBS-induced microbicidal action was completely prevented (FIG. 3C).

Since the microbicidal action of the macrophages was related to the production of $H_2O_2$, an effect of m-3M3FBS on the production of $H_2O_2$ in the mouse neutrophils was examined. The m-3M3FBS increased the production of $H_2O_2$ in the neutrophils in a direction proportional to the concentration (FIG. 3D). In addition, when the neutrophils were preincubated with U-73122, such an effect was significantly decreased (FIG. 3E).

Example 5 m-3M3FBS Inhibits CLP-Induced Apoptosis

Figure 4:
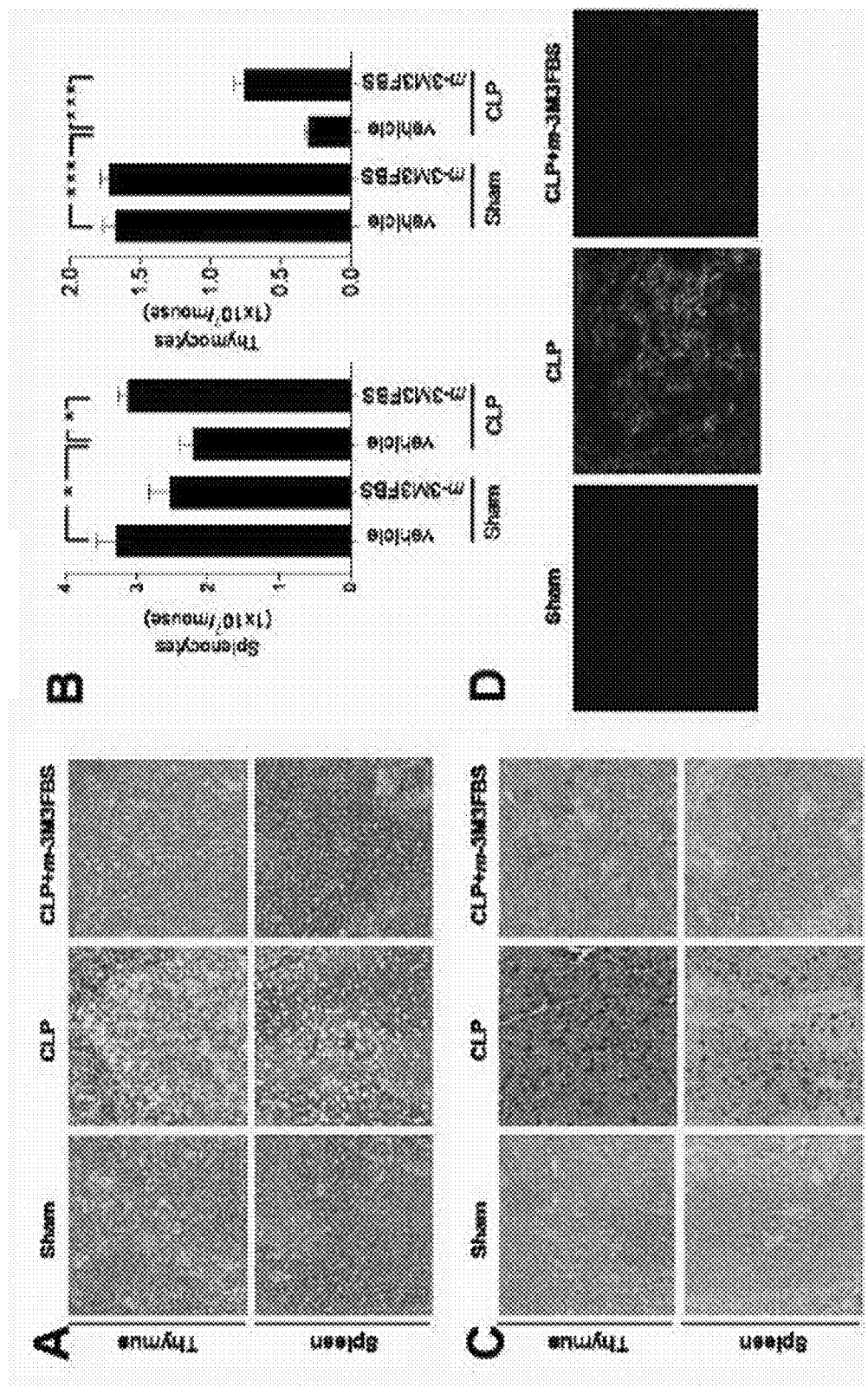
FIG. 4 is a diagram of an effect of m-3M3FBS on the apoptosis of CLP-induced splenocytes by the inhibition of caspase-3 activation. In (A), m-3M3FBS (1.5 mg/kg) was CLP treated and then injected 4 times after 2 and 14 hours. Splenocytes harvested 24 hours after injection of the control, CLP+PBS, and CLP+m-3M3FBS were stained by hematoxylin and eosin staining (magnification, ×100). (B) shows results obtained by counting living splenocytes and thymocytes using a microscope. (C) shows results obtained by performing a TUNEL test on the spleen of a mouse shown in FIG. 4(A). (D) shows results of immunostaining splenocytes of FIG. 4(A) with fragmented caspase-3 antibodies (magnification, ×100). Data was obtained from 8 mice per group (FIGS. 4A, C, and D). Data is represented as average±standard deviations (n=8.

The m-3M3FBS decreased CLP-induced apoptosis of thymocytes and splenocytes. Unlike the control or m-3M3FBS-treated mouse, important morphological changes in apoptotic lymphocytes of the CLP mouse were observed, which were shown as a large number of nuclear fragments and nuclear enrichment (pyknosis) (FIG. 4A). CLP induced apoptosis of the thymocytes and splenocytes. However, such an effect was significantly inhibited when m-3M3FBS was treated (FIGS. 4A and B). The apoptosis of the CLP-induced thymocytes and splenocytes was tested by a DNA fragmentation assay (TUNEL) (FIG. 4C). The injection of m-3M3FBS significantly inhibited CLP-induced apoptosis of the mouse (FIG. 4C). In addition, an indicator of the apoptic splenocytes, that is, activation of caspase-3, was observed. A significant activation of CLP-induced caspase-3 was significantly inhibited by in vivo m-3M3FBS treatment (FIG. 4D).

Example 6

Effect of m-3M3FBS on Production of CLP-Induced Cytokines

Figure 5:
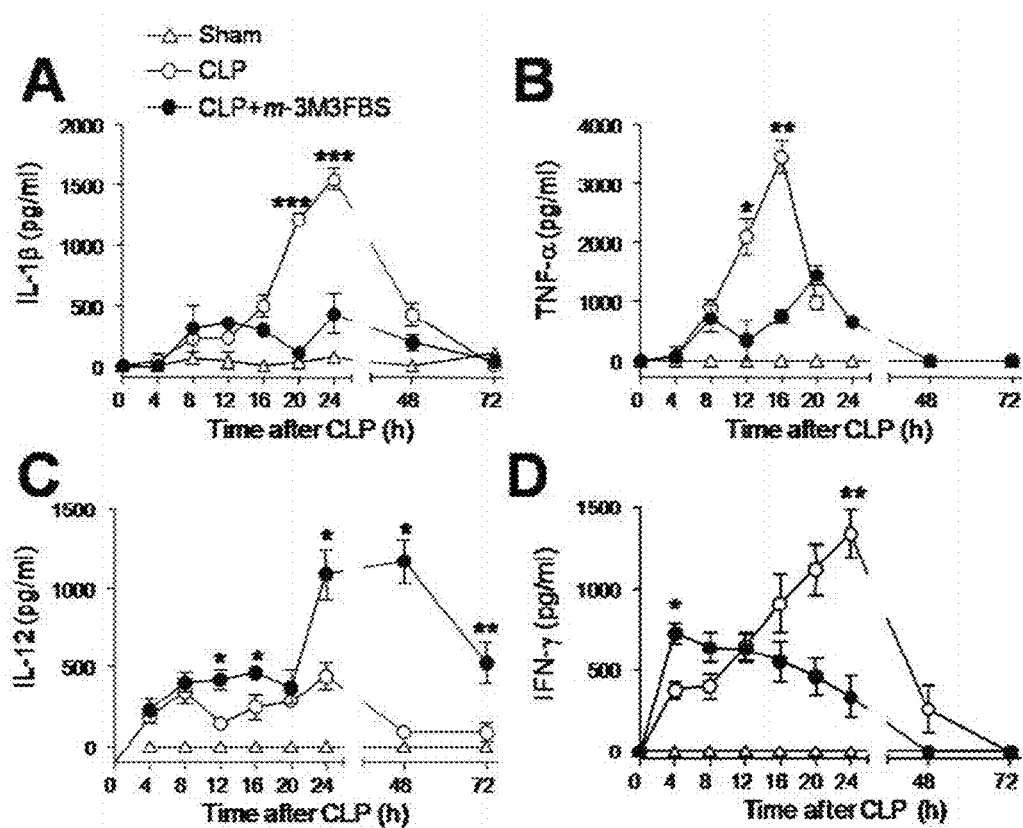
FIG. 5 is a diagram showing an effect of m-3M3FBS on production of CLP-induced cytokines. The m-3M3FBS (1.5 mg/kg) was CLP treated and then subcutaneously injected four times at intervals of 2, 14, 26, 38 hours. The control (sham), CLP+PBS, and CLP+m-3M3FBS were treated to respective animal models. After the CLP treatment, peritoneal fluid was harvested at various intervals, and the content of cytokines was determined by ELISA. Production of IL-1β was shown as A, production of TNF-α was shown as B, production of IL-12 was shown as C, and production of IFN-γ was shown as D. Data is represented as average±standard deviations (n=8, as A and B). Compared with the CLP+PBS, values are at *P<0.05, P<0.01, and *P<0.001.

An effect of m-3M3FBS on production of CLP-induced cytokines in the peritoneal fluid was observed within 4 to 72 hours after CLP (FIG. 5). Proinflammatory cytokines, IL-1β and TNF-α, significantly increased within 24 hours after the CLP (FIGS. 5A and 5B). The m-3M3FBS treatment significantly changed a cytokine level in the CLP model, and the levels of the IL-1β and TNF-α were significantly decreased (FIGS. 5A and 5B). However, the level of T-helper type-1 cytokines, IL-12p70 and IFN-γ was significantly increased when m-3M3FBS was injected (FIGS. 5C and 5D).

Example 7

Effect of m-3M3FBS on Production of LPS-Induced Proinflammatory Cytokines

Since m-3M3FBS inhibited in vivo production of proinflammatory cytokines in an animal model, whether m-3M3FBS directly prevented the LPS-stimulated inflammatory response was tested. After LPS (100 ng/ml) was treated to the mouse neutrophils, production of proinflammatory cytokines was detected. After the LPS treatment, the levels of TNF-α, IL-1β, and IL-6 were decreased more when m-3M3FBS was injected than when LPS was treated to the cells alone (FIG. 6A-C).

Figure 6:
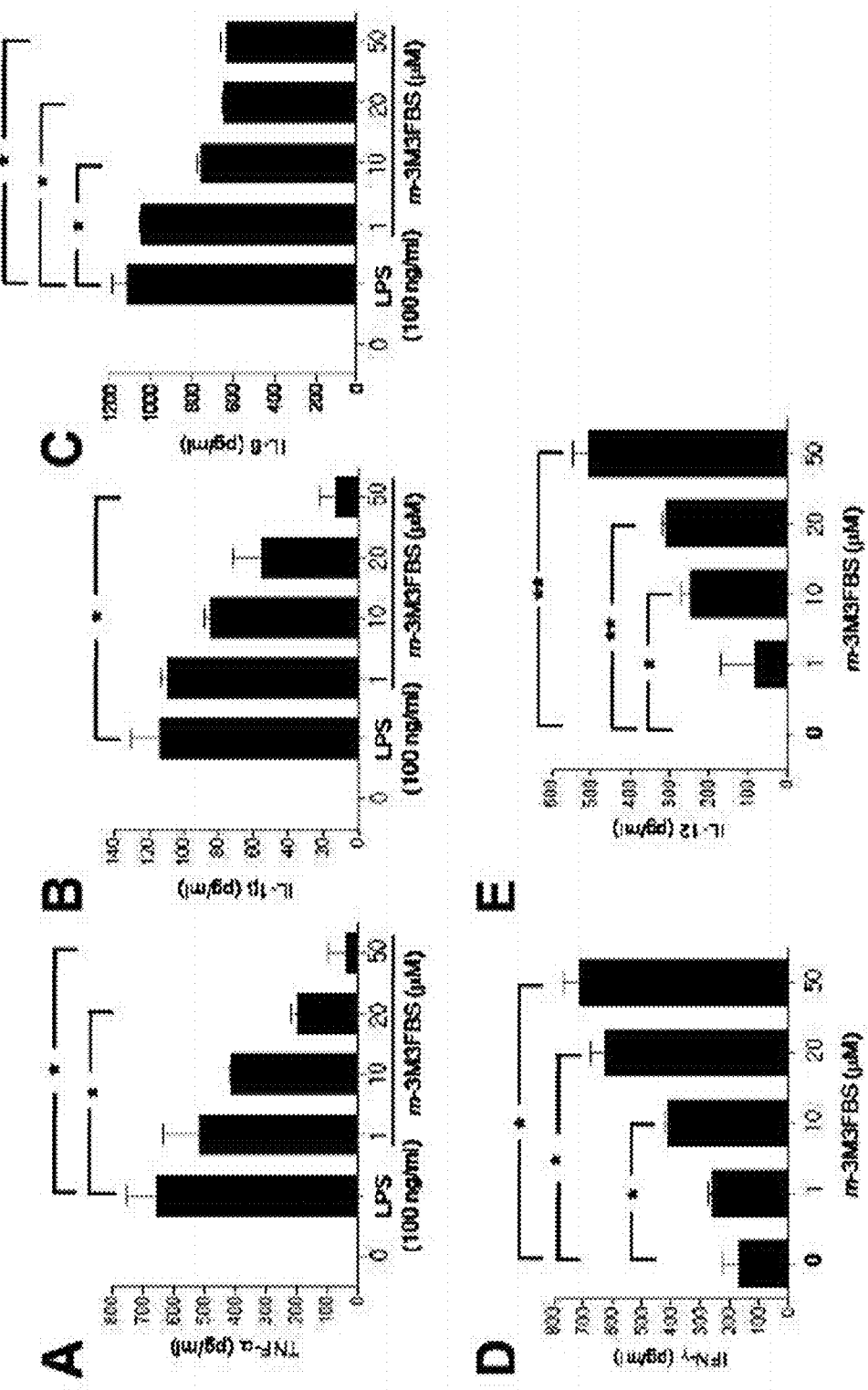
FIG. 6 is a diagram showing a role of m-3M3FBS on in vitro production of cytokines. Neutrophils of mice were preincubated with PBS or m-3M3FBS (10 µm) for 30 minutes, and then treated with PBS or LPS (100 ng/ml) for 3 hours. The levels of IL-1β (A), TNF-α (B), and IL-6 (C) were measured by ELISA. (D-E) are results obtained by treating neutrophils of mice with m-3M3FBS in different concentrations for 3 hours. Levels of INF-γ (D) and IL-12 (E) were measured by ELISA. Data was represented as average±standard deviations (n=8, *P<0.05 and **P<0.001).

The injection of m-3M3FBS increased production of IFN-γ and IL-12 (FIG. 5). Accordingly, whether the m-3M3FBS directly acted on the production of IFN-γ and IL-12 in splenocytes of mice was tested. Various concentrations of m-3M3FBS increased the production of IFN-γ and IL-12 in the splenocytes of mice (FIGS. 6 D and 6E). As a result, it was seen that the m-3M3FBS directly stimulated the production of IFN-γ and IL-12.

To effectively treat or prevent inflammatory diseases and infectious diseases, a composition of the present invention can be effectively used as medicines or health supplements for treating or preventing inflammatory diseases and infectious diseases.

The invention claimed is:

1. A method of treating sepsis or septic shock comprising, administering an effective amount of a composition comprising m-3M3FBS of Formula 1 or a pharmaceutically available salt thereof as an active ingredient

[Formula 1]

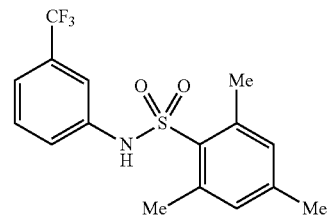

to a subject in need thereof for treating sepsis or septic shock,
wherein the effective amount is about 0.9 to 1.5 mg/kg.

2. The method according to claim 1, wherein the administered effective amount is effective to activate phospholipase C (PLC).

3. The method according to claim 1, wherein the administered effective amount is effective to inhibit microbes, inhibit leukocytes apoptosis, or inhibit LPS-involved signal transduction.

4. The method according to claim 1, further comprising administering a drug selected from the group consisting of anti-inflammatory agents, antipyretic-analgesic agents, blood clotting inhibitors, antibiotics, antimicrobial agents, and antiallergic agents.

5. The method according to claim 1, comprising administering an aqueous solution comprising m-3M3FBS as a sole therapeutic agent, dissolved in a carrier, by injection into the subject.

* * * * *